United States Patent [19]

Mohiuddin

[11] Patent Number: 5,119,675
[45] Date of Patent: Jun. 9, 1992

[54] LIQUID DRAINAGE SYSTEM

[75] Inventor: Mahmood Mohiuddin, Franklin, Mass.

[73] Assignee: The Kendall Company, Mansfield, Mass.

[21] Appl. No.: 567,485

[22] Filed: Aug. 13, 1990

[51] Int. Cl.$^5$ .............. A61B 5/20; B65D 81/00; G01F 3/36

[52] U.S. Cl. ................... 73/223; 73/219; 128/767; 128/771

[58] Field of Search .......... 73/864.51, 219, 864.91, 73/223; 128/760, 761, 767, 771

[56] References Cited

U.S. PATENT DOCUMENTS

| | | | |
|---|---|---|---|
| Re. 30,607 | 5/1981 | Manschot et al. | 128/771 X |
| 3,345,980 | 10/1967 | Coanda | 128/771 X |
| 3,552,395 | 1/1971 | Bidwell et al. | 128/771 X |
| 4,227,413 | 10/1980 | Blum | 73/864.91 X |
| 4,494,581 | 1/1985 | Gordon | 128/761 X |
| 4,554,687 | 11/1985 | Carter et al. | 73/216 X |
| 4,712,567 | 12/1987 | Gille et al. | 128/771 |

FOREIGN PATENT DOCUMENTS

| | | | |
|---|---|---|---|
| 1007533 | 3/1977 | Canada | 128/771 |
| 247958 | 12/1987 | European Pat. Off. | 128/771 |
| 2308511 | 8/1973 | Fed. Rep. of Germany | 128/771 |
| 2259612 | 6/1974 | Fed. Rep. of Germany | 128/771 |
| 2438154 | 2/1975 | Fed. Rep. of Germany | 128/771 |
| 149462 | 7/1981 | German Democratic Rep. | 128/771 |

Primary Examiner—Tom Noland
Attorney, Agent, or Firm—Alvin Isaacs

[57] ABSTRACT

A liquid drainage system is disclosed comprising a combination urine meter element and drainage receptacle, the urine meter element having front and rear walls defining a chamber adapted to receive and measure urine output. The urine meter having an inlet port for receiving urine output from a patient, a drip chamber adapted to direct urine from the inlet port to a burette compartment for measuring urine output situated within the chamber beneath the inlet port, an upper portion of the rear wall having an opening therein for discharging urine from the element, and a deflector adjacent an upper portion of the opening in the element and being tapered toward the opening, whereby to direct urine within the element through the opening when the bottom of the element is raised to direct the urine toward the opening; and a preferably flexible drainage receptacle having front and rear walls joined to define a cavity in the receptacle, the front wall of the receptacle having an opening therein joined in fluid communication with the opening in the rear wall of the urine meter element to permit discharge of urine from the urine meter element to the receptacle, the receptacle having a value for emptying the receptacle.

16 Claims, 3 Drawing Sheets

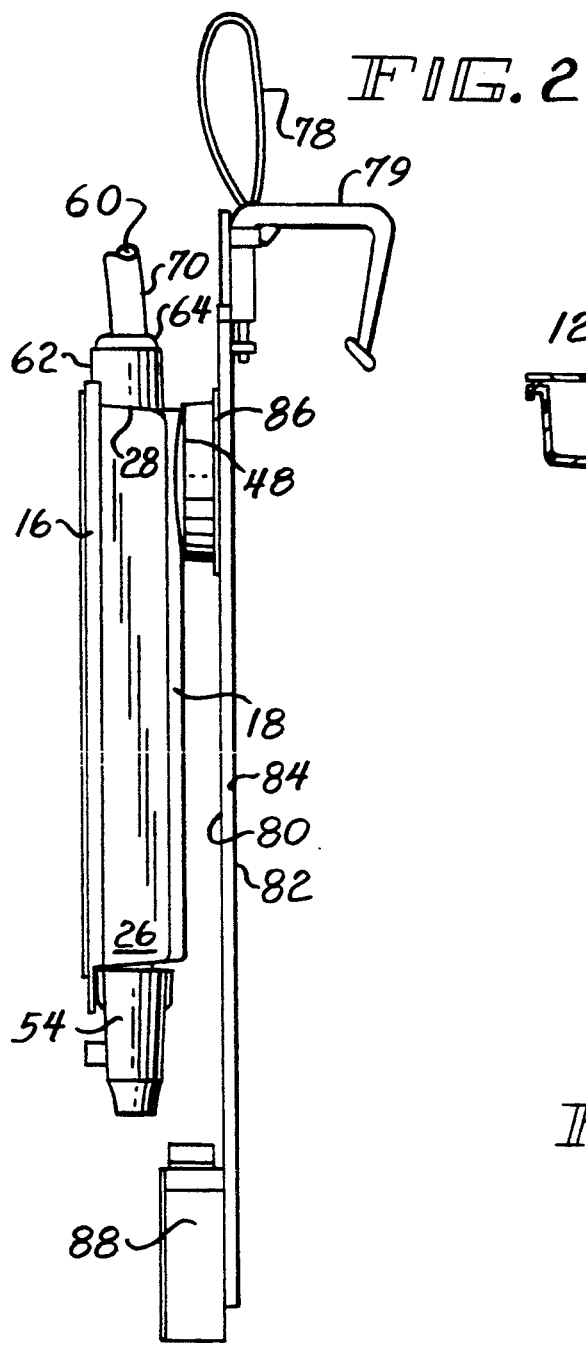
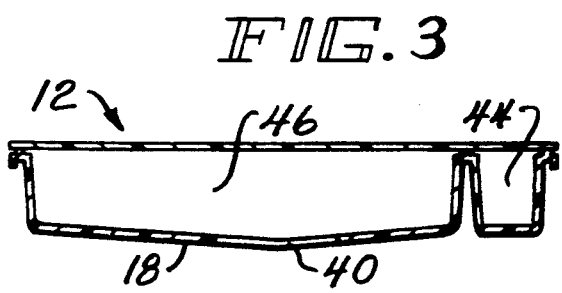
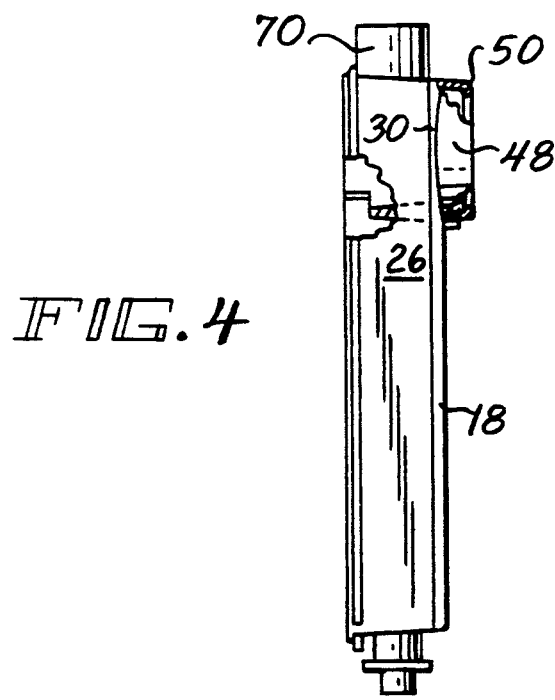
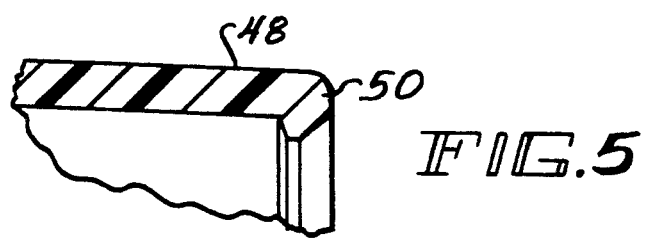

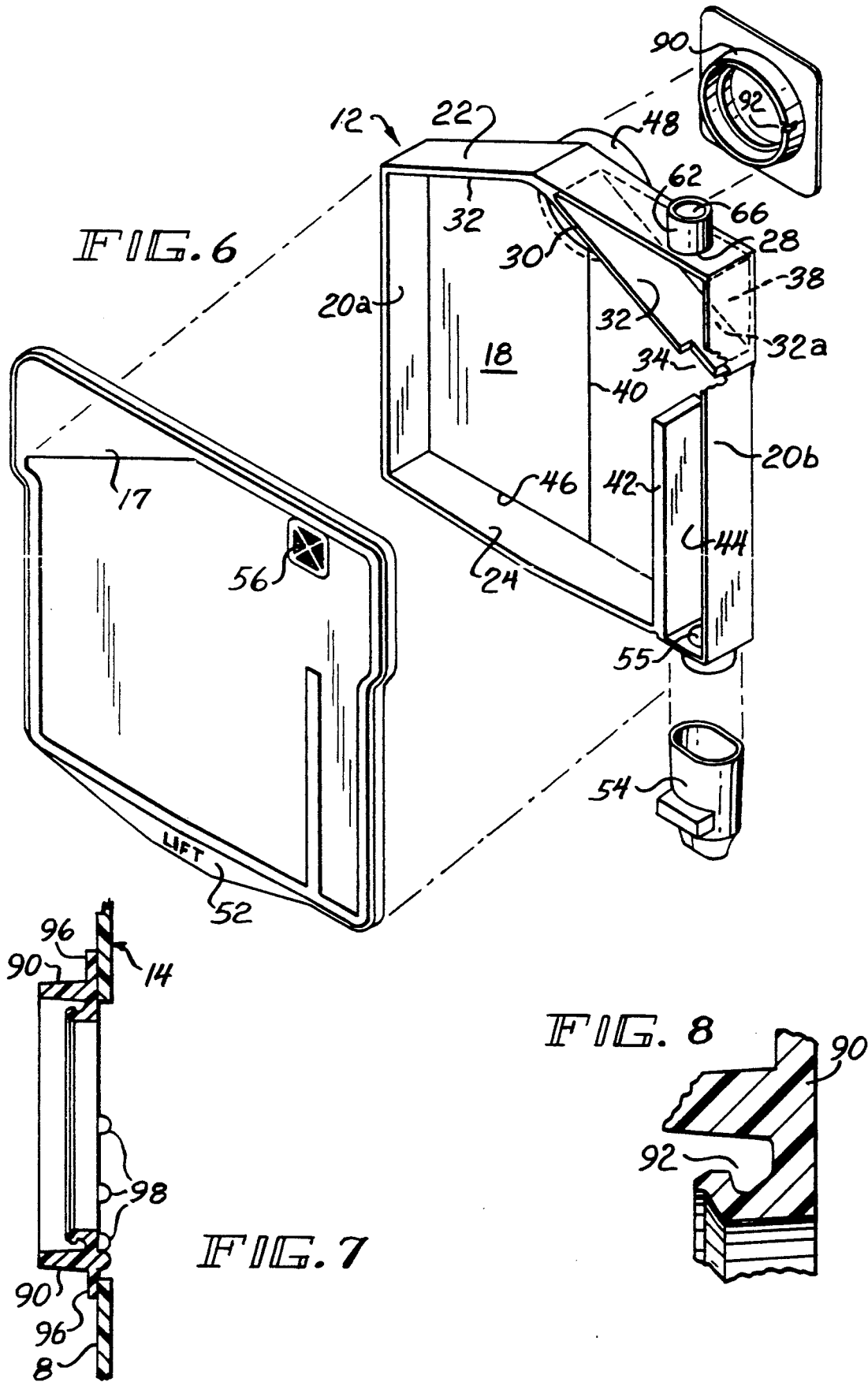

LIQUID DRAINAGE SYSTEM

BACKGROUND OF THE INVENTION

The present invention relates to liquid drainage devices.

Before the present invention, various liquid drainage devices have been proposed for collection and monitoring of urine output. Such drainage devices typically comprise a urine meter element of relatively rigid walls defining a chamber to collect urine from a drainage tube, and a drainage receptacle having a pair of flexible walls in fluid communication with the urine meter. In use, urine collects in the chamber of the urine meter, and after sufficient time, the contents of the meter is dumped into the receptacle through a suitable opening in order to place the urine contents into the receptacle, and then start collection of urine anew in the urine meter. Although such devices have operated satisfactorily, it is desirable to simplify the structure of prior liquid drainage devices and provide improved operation thereof.

SUMMARY OF THE INVENTION

The principal feature of the present invention is the provision of an improved liquid drainage system.

The liquid drainage system of the present invention comprises a urine meter element having a front wall and a rear wall defining a chamber for collection of urine, and an opening in the rear wall. The drainage system also has a drainage receptacle having front and rear walls of flexible material, the front and rear walls being joined to define a cavity in the receptacle, with the front wall having an opening. The drainage system has means connecting the rear wall of the urine meter and the front wall of the receptacle in fluid communication.

A feature of the present invention is that the rear wall of the urine meter element has an outward taper directed toward the front wall of the drainage receptacle.

Another feature of the invention is that the urine meter has a deflector adjacent the upper portion of the urine meter opening and being tapered toward the opening to direct urine through the opening into the drainage receptacle during dumping of urine from the urine meter.

A further feature of the invention is that the tapered rear wall of the urine meter directs the liquid contents of the meter toward the opening during dumping.

A further feature of the invention is that the tapered portion of the meter serves to minimize contact with the receptacle front wall which in turn minimizes the possibility of sticking of the receptacle to the meter after sterilization.

Another feature of the present invention is the provision of an annular protrusion extending outwardly from a rear wall of the urine meter around the opening, with the protrusion having an enlarged annular boss adjacent the outer end of the protrusion, and an annular gasket extending outwardly from the drainage receptacle front wall around the receptacle opening, with the gasket having an annular groove having enlarged an annular inner portion to receive the protrusion and boss receptacle in close engagement.

A further feature in the invention is that the protrusion and gasket cooperate in order to facilitate attachment of the urine meter element to the drainage receptacle.

Another feature of the invention is that the protrusion and gasket lock the receptacle and urine meter together in a simplified and positive manner.

Yet another feature of the invention is that the protrusion and gasket may be bonded together to improve the bond in conjunction with the mechanical locking of the protrusion and gasket.

Still another feature of the invention is that the gasket may have an outwardly directed flange secured to the front wall of the drainage receptacle in order to spread the stresses of the joint between the receptacle and urine meter.

Yet another feature of the invention is that the protrusion and gasket are generally circular in order that the stresses are evenly spread around the juncture of the receptacle and urine meter.

Yet another feature of the invention is that the gasket may have a plurality of space bosses extending inwardly around the gasket in the drainage receptacle opening and being directed toward the receptacle cavity to maintain a separation of the receptacle walls during use of the liquid drainage device. This separation of the walls in turn facilitates emptying the contents of the meter into the drainage receptacle.

Yet another feature of the invention is that the urine meter element may have a lower lift tab in order to lift the element from a lower position to a generally horizontal position during emptying of the contents of the element into the receptacle.

Yet another feature of the invention is that the urine meter may have a front wall comprising a frosted surface on which indicia or legend may be placed.

A further feature of the invention is that the deflector has an end tapering toward a side wall beneath the meter inlet port to define a drip chamber.

Still another feature of the invention is the provision of an annular support member communicating with the inlet port to receive the downstream end of a drainage tube in order to provide strain relief support inhibiting kinking of the drainage tube.

Further features will become more fully apparent in the following detailed description of the embodiments of this invention taken in conjunction with the illustrative drawings and the appended claims.

BRIEF DESCRIPTION OF THE DRAWINGS

In the drawings:

FIG. 2 is a fragmentary side elevational view of the urine meter of FIG. 1;

FIG. 3 is a sectional view taken substantially as indicated along the line 3—3 of FIG. 1;

FIG. 4 is a side elevational view, partly broken away, of the drainage receptacle for the liquid drainage system of FIG. 1;

FIG. 5 is a fragmentary sectional view of an annular protrusion extending from a rear wall of the receptacle of FIG. 4;

FIG. 6 is an exploded perspective view of the urine meter element of FIG. 1;

FIG. 7 is a sectional view of a gasket for the container of FIG. 1; and

FIG. 8 is a fragmentary sectional view of the gasket of FIG. 7 taken on an enlarged scale.

DESCRIPTION OF THE PREFERRED EMBODIMENTS

Figure 1:
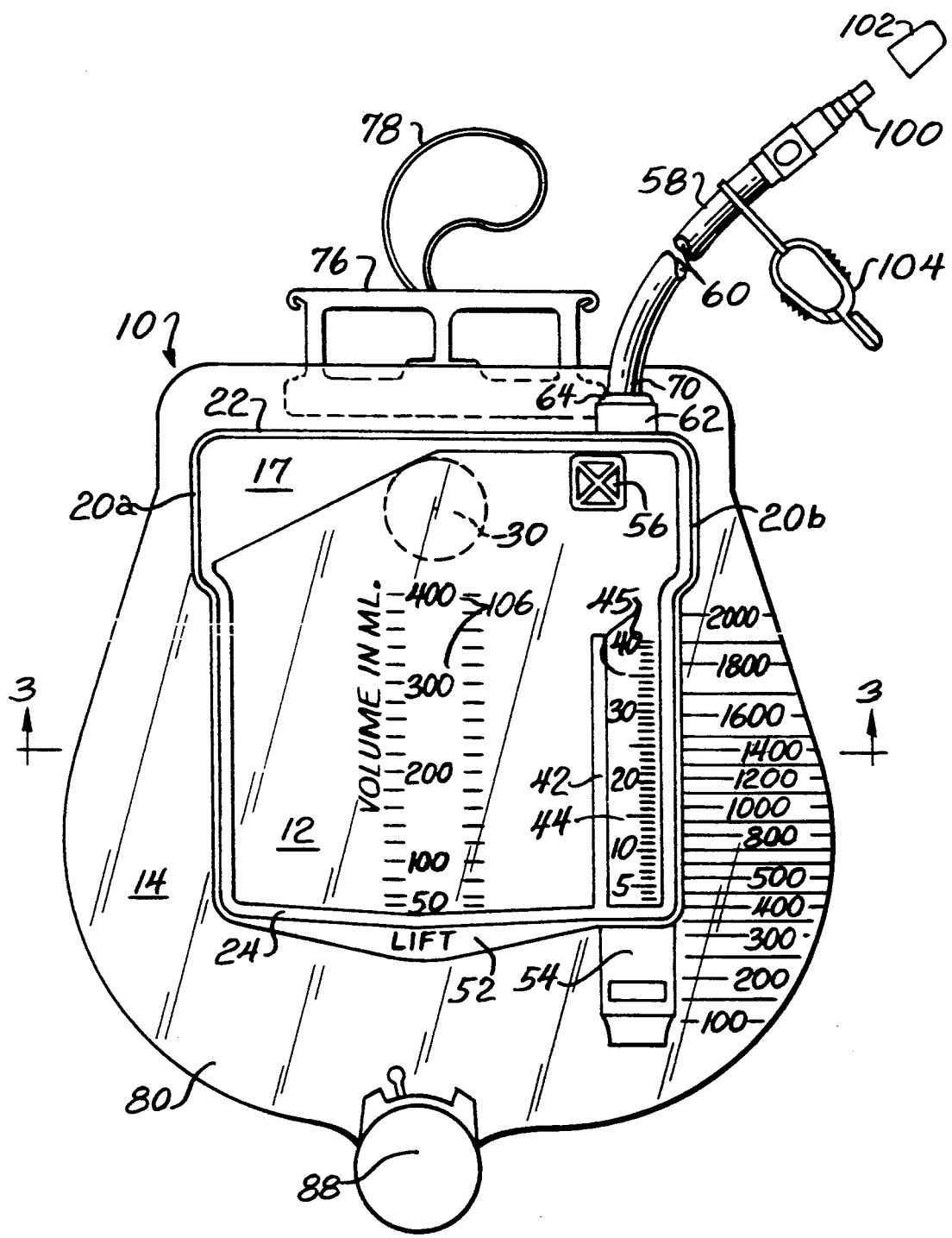
FIG. 1 is a front view of a liquid drainage system comprising a urine meter of the present invention.

Referring now to FIG. 1 and 2, there is shown a liquid drainage system generally designated 10 comprising urine meter element generally designated 12 having relatively rigid walls, such as a suitable plastic material; and a drainage receptacle 14 having a pair of walls, preferable of a flexible material such as polyvinylchloride.

The urine meter 12 has a front wall 16, a rear wall 18, a pair of side walls 20a and 20b, an upper wall 22, and a lower wall 24 defining a chamber 26. Preferably, as shown in FIG. 1, a portion 17 is frosted to permit the clinician to place indicia or relevant data pertaining to the patient.

The urine meter 12 has an inlet port 28 in the upper wall 22 adjacent the side wall 20b to permit passage of urine through the inlet port 28 into the chamber 26. The urine meter 12 has an opening 30 extending through the rear wall 18 adjacent the upper wall 22.

The urine meter 12 has a deflector 32 defining an upper portion of the chamber 16 of the urine meter 12, with the deflector 32 being located adjacent the opening and upper portion of the opening 30, and being tapered downwardly from the upper portion of the opening 30 toward the side walls 20a and 20b. As shown, a portion 32a of deflector 32 extends toward the side wall 20b and has a space from the side wall 20b in order to define an aperture 34 adjacent the side wall 20b at a location below the inlet port 28. The portion of deflector 32 tapering towards side wall 20b defines a drip chamber 38 intermediate the inlet port 28 and aperture 34 communicating with the inlet port 28 and the aperture 34.

As best shown in FIG. 3, the back or rear wall 18 of the meter 12 is tapered downwardly to a longitudinal line 40 of juncture which extends from the lower wall 24 of the meter 12 toward the meter opening 30.

The urine meter 12 has an upright partition 42 extending from the lower wall 24 in the chamber 26 in order to define a relatively small burette compartment 44 located beneath the aperture 34 and drip chamber 38, and a larger compartment 46 located below the opening 30 of the meter 12 to permit overflow from the smaller compartment 44 into the larger compartment 46 during use.

As shown in FIGS. 4 and 5, the meter has an annular protrusion 48 extending from the rear wall 18 of the meter 12 outwardly from the rear wall 18 and extending around the opening 30, with the annular protrusion 48 having an annular inwardly directed boss 50 at an outer end of the protrusion 48.

The meter 12 may have a lower lift tab 52 extending downwardly from the front wall 16 of the meter and being tapered toward the lower central portion of the lift tab 52 to facilitate lifting of the meter for discharge.

The meter 12 may also have a lower valve 54 of known type e.g. a spring-loaded or slide valve, which may be actuated by contact in order to permit drainage of liquid from the compartment 44 of the chamber through opening 55, e.g. for sampling.

The meter may also have a vent 56 extending through the front wall 16 communicating into chamber 38, in order to permit passage of air into the drip chamber 38 and chamber 26 while preventing passage of urine through the vent 56. Preferably, vent 56 will be provided with a per se known bacteria filter in order to prevent ingress of bacteria through the vent.

As shown in FIGS. 1 and 2, the liquid drainage system 10 has an elongated drainage tube 58 having a lumen 60 to permit passage of urine from a patient to the urine meter 12 during catheterization of the patient. With reference to FIG. 4 and 5, the meter has an upstanding annular rim 62 extending upwardly from the upper wall 22 around the inlet port 28 and communicating with the drip chamber 38. As shown, an annular support member 64 is secured, e.g. by solvent bonding, to rim 62. The support member 64 is adapted to receive a downstream end 70 of the drainage tube 58, end 70 being bonded securely to support 64. Thus, the support member 64 provides rigidity for the downstream end 70 of the drainage tube 58 while providing communication between the drainage tube 58 and the drip chamber 38 of the meter 12 through the bore 66, while facilitating attachment of the drainage tube 58 to the meter 12.

The meter 12 may and preferably will include a suitable support device 76 and cord 78 for attachment of the drainage system 10 to a suitable hook or the like. Additionally, as seen in FIG. 1, a hanger hook 79 may be provided for attachment to a bed rail or other such suitable device.

The drainage receptacle 14 has front and rear walls 80 and 82, respectively, preferably of flexible material, with the front wall 80 and rear wall 82 being joined around their periphery in order to define a cavity 84 intermediate the front wall 80 and rear wall 82 to permit collection of liquid therein. As shown, the front wall 80 has an opening 86 in fluid communication with the opening 30 of the urine meter 12, as will be further discussed in detail hereinafter.

The drainage receptacle 14 may have a suitable lower valve 88 which permits drainage of the liquid contents from the cavity 84 during use of the system 10.

As shown in FIGS. 7 and 8, the receptacle 14 has an annular gasket 90 defining an annular groove 92 adapted to receive the annular protrusion 48 and boss 50 of the meter 12 for simplified mechanical engagement of the protrusion 48 and gasket 90 in order to lock the meter 12 to the receptacle 14 in a simplified manner. The protrusion 48 may be solvent bonded to the gasket 90 in order to enhance the bond between the protrusion 48 and gasket 90. The gasket 90 has an outer flange 96 which is bonded to the front wall 80 of the receptacle 14 in order to spread the stresses between the juncture of the meter 12 and receptacle 14, while the protrusion 48 and gasket 90 are generally circular in order to spread the stresses evenly around the juncture between the meter 12 and receptacle 14. As shown, the gasket 90 has a plurality of inwardly directed bosses 98 spaced around a lower portion of the gasket 90 in the opening 86 of the receptacle 14, being directed to the rear wall 82 of the receptacle 14 to maintain separation of the front wall 80 and rear wall 82 of the receptacle 14 during use of the liquid drainage system 10 in order to enhance the communication of fluid through the opening 86 into the cavity 84 during use.

The lift tab 52 may be utilized to raise the urine meter 12 from a lower (vertical or upright) position to a generally horizontal position, and the bosses 98 facilitate in maintaining the separation of the front and rear walls 80 and 82 during the lifting procedure for emptying the meter 12.

During use, a suitable catheter (not shown) is utilized to catheterize a patient, with a proximal end of the catheter located outside the patient's body. A downstream end of the catheter is attached in known manner by means of a per se known catheter adapter assembly 100 in fluid communication to an upstream end of the drainage tube 58 in fluid communication in order to permit drainage of urine through the catheter and the lumen 60 of the drainage tube 58 through the support member 64 into the drip chamber 38. The urine passes through the inlet port 28 into the drip chamber 38, and through the aperture 34 into the lower smaller compartment 48 where it collects with the volume being determined by indicia 45 on the front wall 16 of the meter 12. If desired, the urine may collect in the small burette chamber 44 until it overflows into the larger compartment 46 after sufficient time. Alternatively, the meter may be turned in order to dump the contents of the compartment 44 into the compartment 46 when desired in order to empty the smaller compartment 44 for renewed collection of urine beneath the drip chamber 38.

When no catheter is attached to adapter assembly 100, a suitable cover 102 may be releasably engaged over the free (distal) end. As seen in FIG. 2, a suitable sheet hook 104 may be provided to attach tube 58 to a bed sheet to prevent unwanted movement and possible dislodgement.

However, when it is desired to empty the contents of the meter 12 into the receptacle 14, the lift tab 52 of the meter 12 is grasped in order to lift the meter 12 from a lower upright position to a generally horizontal position while the lowered tapered portion of the back wall 16 of the meter 12 directs the urine in the chamber 26 toward the opening 30 to facilitate passage of urine through the opening 30. Also, the tapered deflector 32 directs the urine through the opening 30 similar to a funnel during the emptying of the meter 12 in order to direct the contents of the meter 12 through the opening 30, the annular protrusion 48, and the annular gasket 90, and the opening 86 of the receptacle 14 into the cavity 84 of the receptacle 14. As previously discussed, the bosses 98 of the gasket 90 facilitate separation of the front wall 80 and rear wall 82 during this time in order to enhance fluid communication between the meter 12 and the receptacle 14.

After the emptying procedure has been completed, the meter is again placed in its upright position to again initiate collection of urine in the meter chamber 26. During the emptying procedure, or at other times, the lower portion 32a of the deflector 32 adjacent the drip chamber 38 prevents the reflux of urine from the chamber 26 into the drip chamber 38 in order to minimize the possibility of possible retrograde movement of bacteria through the drip chamber 38 and drainage tube 58 to the patient with possible deleterious results. During the emptying procedure the lift tab 52 also minimizes the likelihood of inadvertent contact by the clinician with the valve 54 of the meter 12 in order to minimize the possibility of contamination to the valve 54 and enhance the aseptic techniques of the urine meter.

As previously stated, meter 12 has an upper front surface portion 17 which is frosted in order to permit writing a suitable indicia or legends for recording patient information, such as the date and time when collection of liquid has been initiated. As shown in FIG. 1, the meter 12 may also have indicia 106 in order to indicate the volume of liquid collected in the larger compartment 46.

In accordance with the present invention, the protrusion 48 and gasket 90 permit attachment of receptacle 12 and container 14 in a simplified manner in order to provide an improved mechanical locking of the receptacle 12 and container 14.

The particular materials employed in the manufacture of the urine meter and drainage receptacle components of this invention will be readily apparent to those skilled in the art and will generally be selected from these polymeric materials heretofore employed in the art. As will be readily appreciated, at least the front wall 16 of the meter must be sufficiently transparent to reveal the urine contents thereof. As shown in FIG. 1, the front wall of the drainage bag is also preferably provided with volumetric indicia, in which event it should also be transparent to permit measurement of its contents.

From the foregoing description and illustrative drawings, it will be seen that the present invention provides an elegant new liquid drainage system affording significant advantages over the general state of the art.

While there is a tendency for some residual fluid to remain after emptying of the prior devices, the novel design of the present invention permits full emptying of the meter into the drainage receptacle. Additionally, this emptying action is accomplished in a way which precludes wetting and subsequent clogging of the vent filter, an inherent problem in prior devices.

By way of recapitulation, it will be seen that the novel design features of this invention provide further important advantages, including the following:

(1) simplified emptying of the meter liquid contents into the drainage receptacle in a manner which precludes unwanted re-entry of the liquid contents back into the meter;

(2) the provision of the gasket bosses 98 to maintain separation of the receptacle walls, thus insuring a cavity or chamber for easy dumping of the meter contents;

(3) deflector walls 32 funneling the urine towards the opening for dumping, which walls serve the additional purpose of protecting the vent from wetting and also for preventing urine from getting into the drip chamber during emptying;

(4) the drip former position is such that it always permits the urine to go into the burette chamber first, irrespective of the angle of the device;

(5) the drip chamber wall with aperture does not permit urine from retrograding back;

(6) providing a frosted area on the meter for inscribing relevant data;

(7) the convenient and "user-friendly" lift tab which also inhibits chances of contamination during emptying;

(8) the strain relief manner in which the downstream end 70 of the tube communicates with the device, thus preventing kinking; and (9) preferably providing the protrusion 48 and gasket 90 in a generally circular configuration, which configuration serves to spread the stresses evenly around the juncture between the meter and drainage receptacle.

Since various changes may be made without departing from the scope of the invention herein contemplated, it is intended that all matter contained in the foregoing description and drawings shall be taken as illustrative and not in a limiting sense.

What is claimed is:

1. A liquid drainage system comprising, in combination:

a urine meter element having front, rear, top, bottom and side walls defining a chamber adapted to receive and measure urine output, an inlet port communicating with said chamber for receiving urine input, an opening in said rear wall for discharging urine from said chamber, and deflector means adjacent to an upper portion of said opening said tapered toward said opening, whereby to funnel urine from said chamber through said opening when the bottom of said meter is elevated to direct urine to be discharged toward said opening, means defining a drip chamber for urine entering said meter through the inlet port, and vent means permitting ingress of air to within the drop chamber and the chamber of the urine meter adapted to receive the measure urine output, the deflector means further providing means protecting the vent means against wetting during emptying of the urine meter chamber;

a drainage receptacle having front and rear walls joined to define a cavity in said receptacle adapted to receive and retain urine discharged from said urine meter, said front wall of said receptacle having an opening therein; and means connecting said rear wall of said meter and said front wall of said receptacle in fluid communication through the openings.

2. A liquid drainage system as defined in claim 1 wherein the rear wall of said urine meter has an outward taper directed toward the front wall of said drainage receptacle, whereby to minimize contact of said urine meter element with the front wall of said drainage element during use.

3. A liquid drainage system as defined in claim 2 wherein said contact is along a longitudinal line of juncture extending from said bottom wall toward said opening in said meter.

4. A liquid drainage system as defined in claim 1 wherein said connecting means comprises an annular protrusion extending outwardly from said rear wall of said meter opening, said protrusion having an enlarged annular boss adjacent an outer end of said protrusion; and an annular gasket extending outwardly from said front wall of said drainage receptacle around said receptacle opening, said gasket having an annular groove adapted to receive said annular protrusion and boss, whereby to provide mechanical engagement of said protrusion and gasket and thereby to secure said meter to said receptacle.

5. A liquid drainage system as defined in claim 4 wherein said protrusion and said gasket are of a generally circular configuration whereby to spread stresses evenly around the juncture between said urine meter element and said drainage receptacle.

6. A liquid drainage system as defined in claim 4 wherein said gasket has a plurality of space bosses spaced apart extending inwardly toward said cavity within said drainage receptacle, whereby to maintain a separation of said receptacle walls.

7. A liquid drainage system as defined in claim 4 wherein said protrusion is chemically bonded to said gasket, whereby to enhance the bond beyond that obtained by the mechanical engagement of said protrusion and gasket.

8. A liquid drainage system as defined in claim 1 wherein at least the portion of said front wall of said urine meter opposite said drip chamber is transparent to permit a clinician to observe urine dripping through said inlet port.

9. A liquid drainage system as defined in claim 1 including means communicating a drainage tube for said urine to said inlet port.

10. A liquid drainage system as defined in claim 9 wherein said communicating means includes support means providing a strain relief whereby to inhibit kinking of said drainage tube.

11. A liquid drainage system as defined in claim 1 wherein said deflector means further provides means for preventing urine from getting into said drip chamber during emptying.

12. A liquid drainage system as defined in claim 1 wherein said chamber of said urine meter contains a burette compartment situated beneath said inlet port, said compartment being provided with visible volumetric indicia for measuring the quantity of urine input within said compartment.

13. A liquid drainage system as defined in claim 12 including means for discharging urine within said compartment to said chamber.

14. A liquid drainage system as defined in claim 13 including means defining a drip chamber disposed between said inlet port and said compartment, said drip chamber communicating with said compartment whereby urine entering said meter through said inlet port drips down into said compartment for measurement.

15. A liquid drainage system as defined in claim 14 wherein said means defining a drip chamber is so positioned between said inlet port and compartment such that urine entering through said inlet port will always pass into said burette chamber, irrespective of the angle of said meter.

16. A liquid drainage system as defined in claim 1 wherein the vent means is provided with a bacteria filter to prevent ingress of bacteria through the vent means.

* * * * *

UNITED STATES PATENT AND TRADEMARK OFFICE
CERTIFICATE OF CORRECTION

PATENT NO. : 5,119,675
DATED : 06/09/92
INVENTOR(S) : Mahmood Mohiuddin

It is certified that error appears in the above-indentified patent and that said Letters Patent is hereby corrected as shown below:

Col. 7, line 7 "said" should be -- and --;

line 14, "drop" should be --drip--; and line 16, "the" (first occurrence) should be -- and --.

Signed and Sealed this

Second Day of November, 1993

Attest:

BRUCE LEHMAN

Attesting Officer

Commissioner of Patents and Trademarks